United States Patent
Isobe et al.

(10) Patent No.: US 8,833,186 B2
(45) Date of Patent: Sep. 16, 2014

(54) SAMPLE CONVEYING SYSTEM

(75) Inventors: Tetsuya Isobe, Hitachinaka (JP);
Hiroshi Ohga, Hitachiomiya (JP);
Masaaki Hanawa, Hitachinaka (JP);
Tatsuya Fukugaki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 245 days.

(21) Appl. No.: 13/384,833

(22) PCT Filed: Sep. 8, 2010

(86) PCT No.: PCT/JP2010/065434
§ 371 (c)(1),
(2), (4) Date: Jan. 27, 2012

(87) PCT Pub. No.: WO2011/040196
PCT Pub. Date: Jul. 4, 2011

(65) Prior Publication Data
US 2012/0266698 A1    Oct. 25, 2012

(30) Foreign Application Priority Data

Sep. 30, 2009   (JP) ................................ 2009-225923

(51) Int. Cl.
*G01N 1/20* (2006.01)
*G01N 35/02* (2006.01)
*G01N 35/04* (2006.01)
*G01N 35/00* (2006.01)

(52) U.S. Cl.
CPC ...... *G01N 35/026* (2013.01); *G01N 2035/0415* (2013.01); *G01N 35/04* (2013.01); *G01N 2035/0406* (2013.01); *G01N 2035/00801* (2013.01); *G01N 2035/0467* (2013.01)
USPC ........................................................ 73/863.92

(58) Field of Classification Search
CPC ......... B56G 47/48; G01N 35/02; G01N 35/04
USPC ........................................ 73/863.91, 863.92
See application file for complete search history.

(56) References Cited

U.S. PATENT DOCUMENTS

2008/0170967 A1 *  7/2008  Itoh .............................. 422/104
2009/0191095 A1    7/2009  Nakamura

FOREIGN PATENT DOCUMENTS

JP    08-220102    8/1996
JP    09-033539    2/1997
(Continued)

OTHER PUBLICATIONS

English Machine Translation of Kojo et al., JP 09-208044, Aug. 12, 1997, Translated Jan. 23, 2014.*

(Continued)

*Primary Examiner* — Hezron E Williams
*Assistant Examiner* — David Z Huang
(74) *Attorney, Agent, or Firm* — Mattingly & Malur, PC (57) ABSTRACT

Conventional conveying lines have required building according to the particular shapes of test tube racks and test tube holders. For this reason, at least two types of dedicated lines, one for test tube racks and one for test tube holders, have been needed in one system, so there has been a tendency for systems to be complex in structure and disadvantageous in cost. To solve these problems, this invention provides a sample conveying system designed so that test tube racks and test tube holders can move on the same line, and high in both cost-effectiveness and reliability.

8 Claims, 4 Drawing Sheets

(56) References Cited

FOREIGN PATENT DOCUMENTS

| | | |
|---|---|---|
| JP | 09-054096 | 2/1997 |
| JP | 09-208044 | 8/1997 |
| JP | 11-083865 | 3/1999 |
| JP | 2002-181835 | 6/2002 |
| JP | 2009-180607 | 8/2009 |

OTHER PUBLICATIONS

English Machine Translation of Fukugaki et al., JP 2002-181835, Jun. 26, 2002, Translated Jan. 23, 2014.*
English Machine Transaltion of Nakamura, JP 2009-180607, Aug. 13, 2009, Translated Jan. 24, 2014.*

* cited by examiner

SAMPLE CONVEYING SYSTEM

TECHNICAL FIELD

The present invention relates to a technique used in sample conveying systems to convey samples of blood and the like so that the samples are later divided, dispensed or analyzed.

BACKGROUND ART

Test tubes that accommodate samples of blood and the like are each made of glass or a resin. The samples accommodated in these test tubes are commonly mounted on vertically retainable test tube racks and test tube holders and conveyed using conveyance belt lines.

In addition, diverse holders and racks have heretofore been devised for retaining test tubes of different sizes and lengths.

To convey these diverse test tube racks and test tube holders, it has been necessary to change the widths and shapes of existing conveyance lines according to the shapes and sizes of the test tube racks and holders to be conveyed, and build new conveying lines.

A known, dedicated conveying system for test tube holders is described in Patent Document 1.

PRIOR ART LITERATURE

Patent Document

Patent Document 1: JP-1996-220102-A

SUMMARY OF THE INVENTION

Problems to be Solved by the Invention

Conventional conveying lines have required building according to the particular shapes of test tube racks and test tube holders. For this reason, at least two types of dedicated lines, one for test tube racks and one for test tube holders, have been needed in one system, so there has been a tendency for systems to be complex in structure and disadvantageous in cost.

In addition, depending on the installation locations for analyzers to which the test tube racks and holders are to be supplied, the necessity may arise to make at least the two lines cross each other. If this is the case, it is necessary that at least one line be routed over the other line by providing a conveying line changer mechanism or the like, or that at least one line be passed through below the other line by adding an elevator mechanism or the like. Providing these mechanisms has also been likely to make the system complex and expensive.

Means for Solving the Problems

In order to solve the foregoing problems, the present invention enables test tube racks and test tube holders to move through the same conveying line, by changing a part of each test tube rack or holder into a shape of an equal dimension. For example, a test tube rack has a rectangular three-dimensional construction and capable of accepting at least five test tubes, while a test tube holder has a columnar three-dimensional construction, constructed from a large-diameter column and a small-diameter column and capable of accepting at least one test tube. Even the test tube rack and the test tube holder thus constructed can move through the same conveying line, provided that width of the rack and the diameter of the smaller column of the holder are preset to be equal and that the conveying line is constructed so as to have its width increasable by nearly 1 to 2 mm above that presetting. In this case, since the test tube holder could overturn during conveyance, there is a need to add an overturn preventing structure at the conveying line side.

The particular conveying line can automatically discriminate the different shapes of the test tube rack and the test tube holder. In addition, if the test tube rack and the test tube holder each have an ID tag or equivalent storage medium mounted on the rack or holder, the line can supply the test tube rack and the test tube holder to a desired analyzer while communicating with a system.

Effects of the Invention

The present invention provides a sample conveying system intended to:

(1) automatically supply sample-containing test tube racks and test tube holders, both being test tube carriers of different shapes, to an analyzer through one conveying line, (2) minimize manufacturing costs since automatic execution of above item (1) enables each test tube carrier to be supplied using one dedicated conveying line, (3) make it unnecessary, because of automatic execution of item (1), for at least one of a plurality of conveying lines to be routed over the other lines by providing a conveying line changer mechanism or equivalent, or to be passed through below the other lines by adding an elevator mechanism or equivalent, and also change a traveling direction of the conveying line flexibly to leftward and rightward directions.

MODE FOR CARRYING OUT THE INVENTION

Hereunder, an embodiment of the present invention will be described with reference to the accompanying drawings.

The present embodiment applies to one specific configuration of a sample conveying system whose constituent elements can be combined in various forms.

Figure 1:
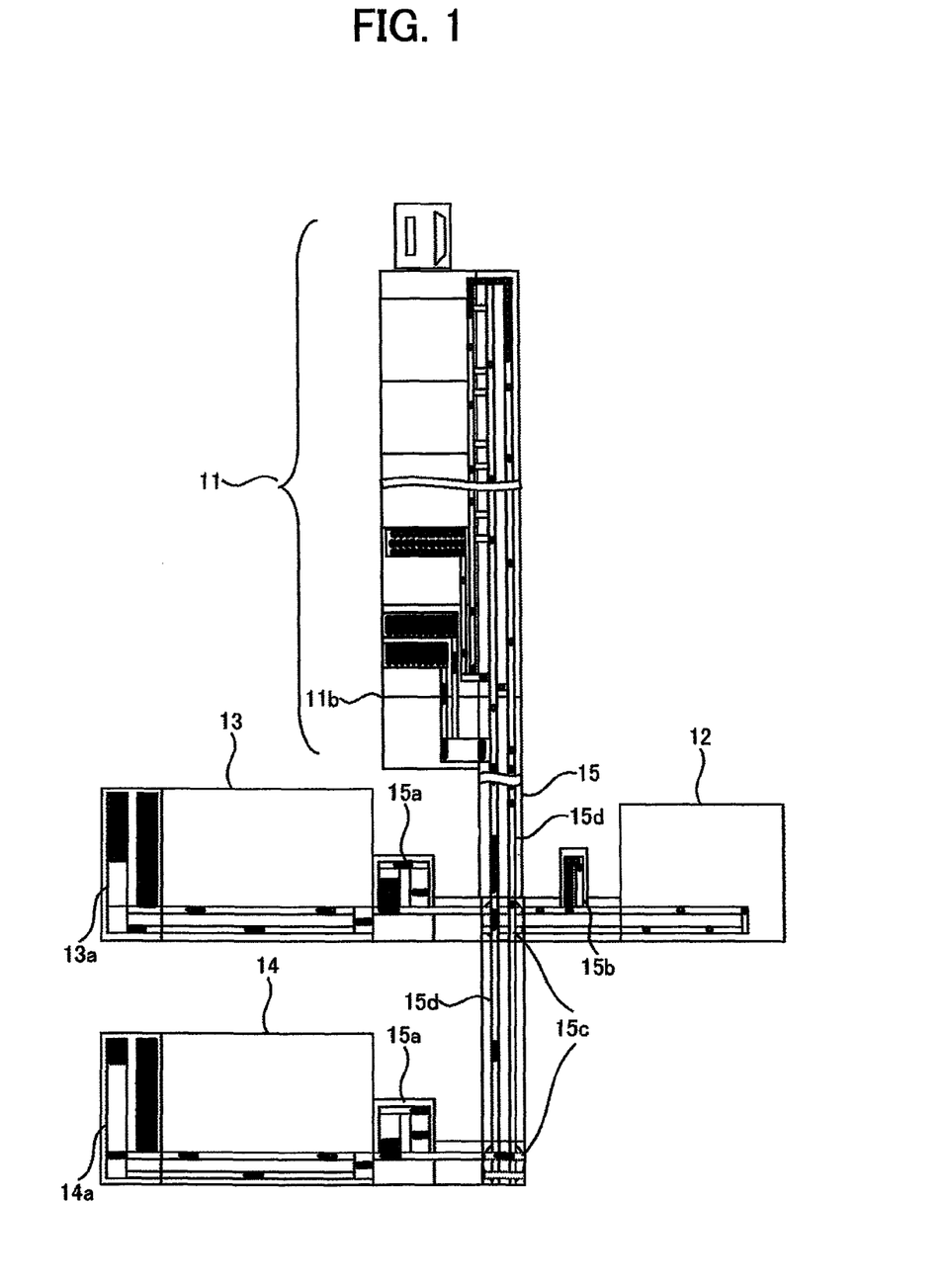
FIG. 1 is a schematic diagram of a sample conveying system.

The sample conveying system 11 is usually constituted by a plurality of units, which include a loading unit, a centrifugal separating unit, a decapping unit, a BCR unit, a sample dispensing unit, a capping unit, a storage unit, and the like.

Sample-containing test tubes that have been loaded into the system are mounted on test tube holders 21, which are then supplied to each unit through a conveying line in the system.

Usually, the test tube holders 21 supply the sample-containing test tubes to each unit while moving about in the sample conveying system. Under a specific operational architecture, however, each test tube holder 21 may be supplied to analyzers. The test tube holder 21 has a mounted storage medium onto which an RFID and other information can be stored, and this test tube holder moves while communicating with the system via antennas 24a to 24f.

Figure 2:
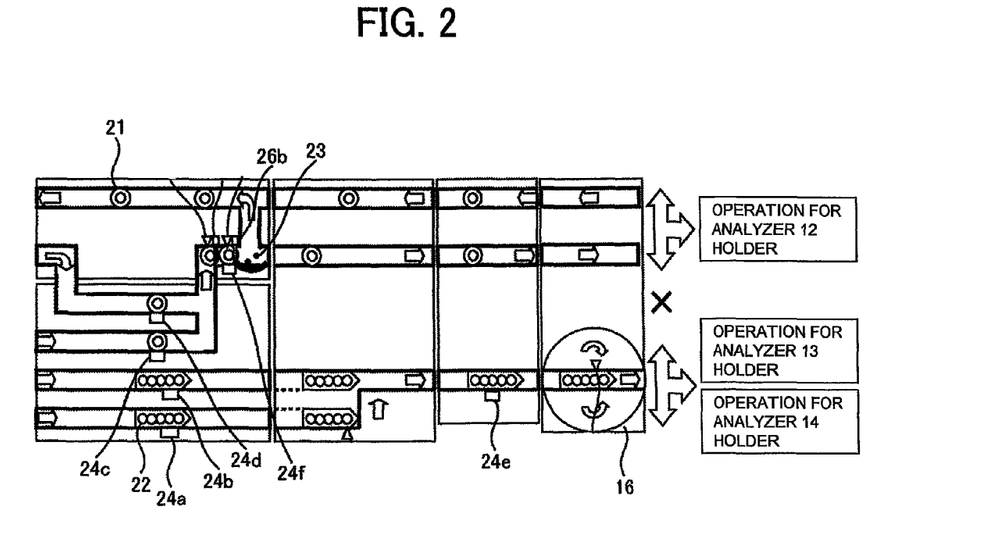
FIG. 2 is a schematic diagram of an independent-line arrangement for conveying test tube racks and test tube holders via different kinds of lines.
Figure 3:
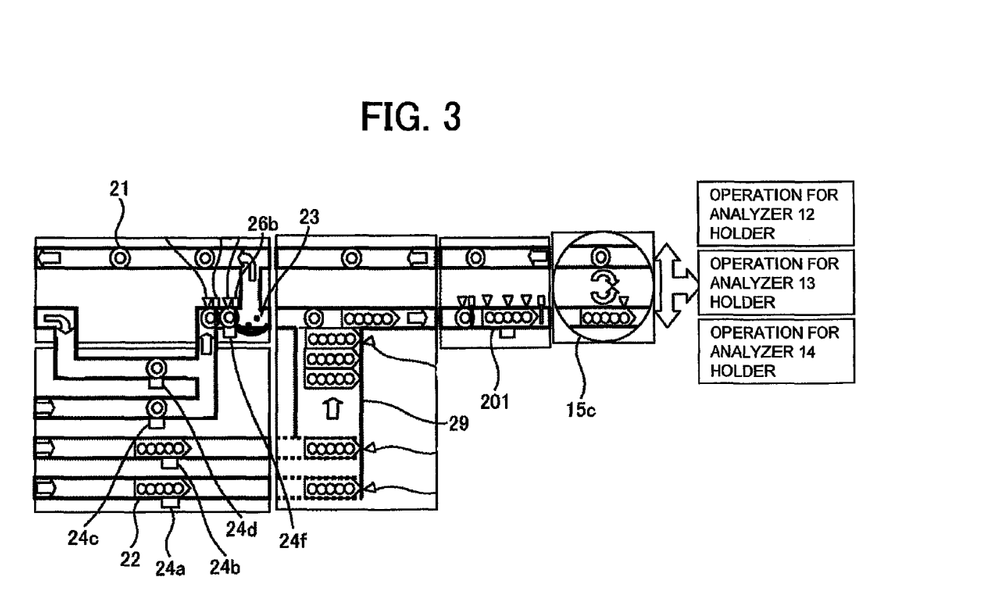
FIG. 3 is a schematic diagram of a mixed-line arrangement for conveying both test tube racks and test tube holders in mixed form using one kind of line.

FIGS. 2 and 3 are schematic diagrams of the system configuration ranging between the sample dispensing unit 11b and each analyzer inclusive.

The sample dispensing unit 11b suctions a sample from any one of the sample-containing test tubes mounted on the test tube holder 21, dispenses the sample in smaller quantities into sample cups or other test tubes. If the sample inside the test tube mounted on the test tube holder 21 is referred to as a parent sample, the samples in the sample cups or other test tubes are child samples.

The following description envisages dispensing the suctioned sample in smaller quantities into the sample cups mounted on a test tube rack 22. The test tube rack 22 has a mounted storage medium onto which an RFID and other information can be stored, and this test tube rack moves while communicating with the system via the antennas 24a to 24f.

Referring to FIG. 2, the test tube rack with the child samples placed thereupon communicates with the antennas 24a and 24b, and after acquiring information from the system, starts moving towards the analyzers 13 and 14 specified in the information.

The test tube rack 22 passes through a rack conveying section in the system and then moves along a dedicated conveying line for racks.

Meanwhile, the test tube holder 21 from which the sample has been dispensed into the sample cups communicates via the antenna 24d, then acquires information such as whether the test tubes containing the parent sample are to be returned to the storage unit or headed for an analyzer 12, and starts moving towards the destination.

Upon reaching a branching point, the test tube holder 21 comes to a temporary stop at a stopper 26b and communicates here via the antenna 24f. The destination has its direction determined by a branching mechanism 23.

If the test tube rack 22 that moves along the rack-dedicated conveying line is to head for the analyzer 13, the rack needs to have its moving direction changed via a dedicated rotating mechanism for test tube racks 16. For this reason, the rack exchanges information with the system via the antenna 24e in front of the dedicated rotating mechanism for test tube racks 16, changes the direction via the dedicated rotating mechanism for test tube racks 16, and moves to a conveying line leading to the analyzer 13.

The test tube rack 22 that has moved to the analyzer 13 is stored into a rack storage section 13a of the analyzer 13 upon completion of analysis.

The direction of the test tube holder 21 which moves along a holder-dedicated conveying line and heads for the analyzer 12 can be changed using an equivalent of the branching mechanism 23.

The test tube holder 21, however, needs to be returned through a test tube returning line 15d, since there is a need for the sample conveying system of the present embodiment to store the parent sample mounted on the test tube holder 21 into the storage unit.

The above has described the movements of the test tube rack 22 and test tube holder 21 that relate to FIG. 2. One problem associated with the scheme of FIG. 2 is that the number of conveying lines required is at least three, inclusive of the holder returning line. In this case, a necessary number of mechanisms increases and the system size increases accordingly. The system also becomes disadvantageous in cost.

Another problem is that installation positions for the analyzers are limited. In the scheme of FIG. 2, these installation positions for the analyzers 13 and 14 that use the test tube rack 22 are usually the front or the right to the traveling directions of the analyzers, and for the analyzer 12 that uses the test tube holder 22, the front or the left to the traveling directions.

If it is absolutely necessary to install the analyzers side by side in the same direction, this is possible by arranging in fixed order the analyzers that use the test tube rack 22, and the analyzer that uses the test tube holder 21, but flexible layout of these analyzers is impossible at any rate.

Least of all, for a left-right interchange of the analyzers 12 and 13, is there no way other than to reroute at least one of the lines over the other line(s) by providing a conveying line changer mechanism or equivalent, or to pass the line through below the other line(s) by adding an elevator mechanism or equivalent. This way will cost too much to be realistic.

With these problems in mind, the best mode is shown in FIG. 3.

FIG. 3 shows construction in which the test tube rack 22 and the test tube holder 21 move through the same conveying line.

After passing through the rack conveying section in the system, the test tube rack 22 and test tube holder 21 with the sample-containing test tubes or sample cups mounted thereupon are supplied through a conveying line 15 connected to each analyzer. The system, however, is constructed so that the test tube rack 22 and the test tube holder 21 can both pass through the same conveying line 15. This construction reduces the number of conveying lines to two, thus establishing a simple conveying line arrangement, and yielding an advantage in cost.

Figure 4:
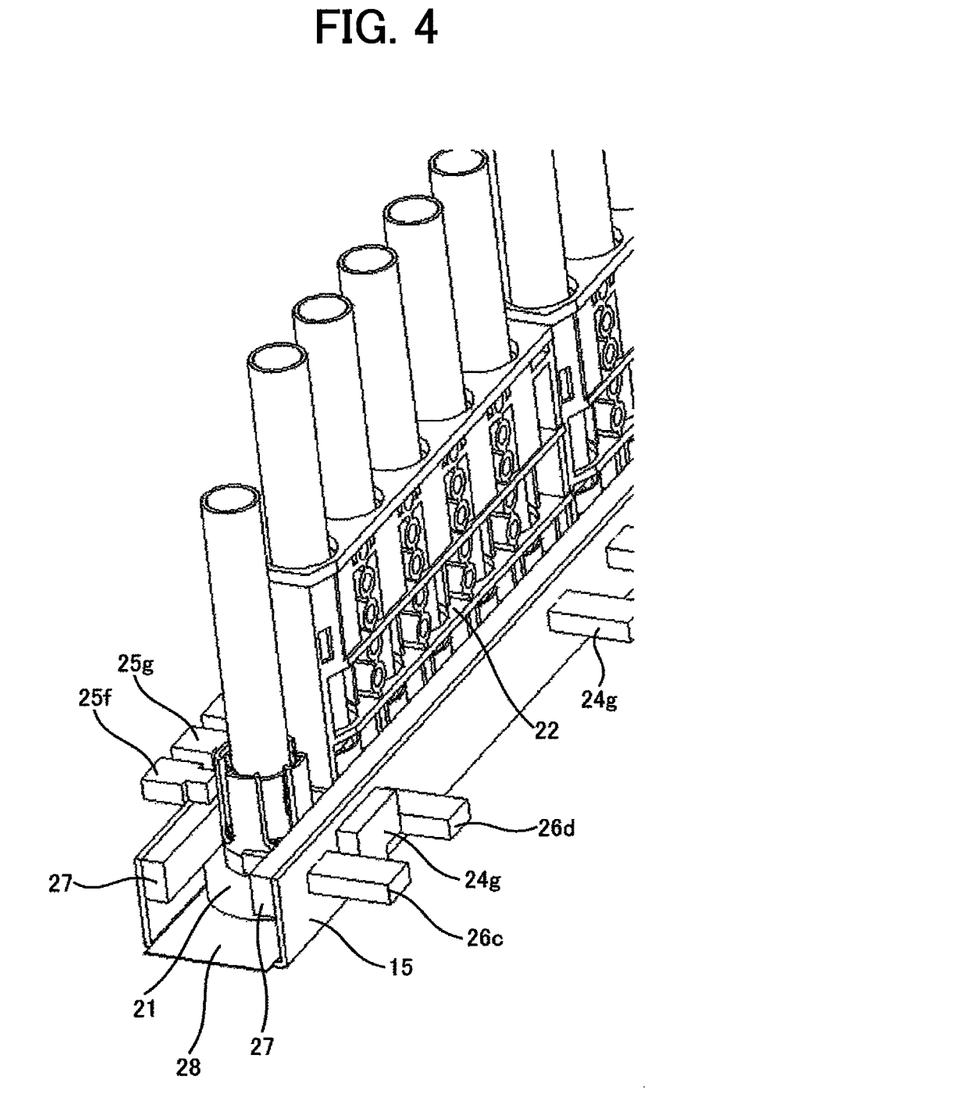
FIG. 4 is a schematic structural view showing a moving state of test tube racks and test tube holders on a conveying line.

FIG. 4 is a simplified structural view of the conveying line 15, test tube racks, and test tube holders. Width of the test tube rack 22 and a smaller-diameter section of the test tube holder 21 are the same dimension, such that the system can use conveying lines of the same width as the particular dimension.

The conveying line 15 is provided with guides 27 to add a function that prevents the test tube holder 21 from overturning.

The line is metallic, and the guides 27 can also be metallic or can otherwise be formed from a resin or the like. The same function will also be performed, even if the line and the guides are manufactured integrally by extrusion molding or the like.

The test tube rack 22, which is basically a conventional rack, is constructed so that at least five test tubes can be mounted, and is fitted with a storage medium onto which information can be stored. Bar-codes, for example, can be an alternative to the storage medium.

The test tube holder 21 is constructed to have a hollow cylindrical shape, enabling a test tube to be mounted in a hollow central section of the circle. The construction is a combination of a small-diameter cylindrical section and a large-diameter cylindrical section which forms part of the guides 27 to prevent overturning, and the small-diameter cylindrical section is of the same dimension as the width of a test tube rack.

The movements of the test tube rack 22 and the test tube holder 21 along the conveying line 15 are described in further detail below. The test tube rack 22 and the test tube holder 21 move along the same line by means of a test tube rack moving mechanism 29 provided on the sample dispensing unit 11b.

At this time, the test tube rack 22 is loaded before the test tube holder 21 coming closer at a spatial interval arrives at a meeting point. Collisions between the holder and rack at this time are avoided since the system uses sensors or the like to control positions of the holder and rack.

Upon joining at the meeting point, the test tube rack 22 and the test tube holder 21 start to move towards specified respective analyzers, at which time, the rotating mechanism for rotating a test tube rack and a test tube holder 15c or equivalent also needs to be used to change the traveling directions of the two carriers.

The rotating mechanism for rotating a test tube rack and a test tube holder 15c is constructed to be sharable between the test tube rack 22 and the test tube holder 21, and rotates at high speed in two directions.

The rotating mechanism for rotating a test tube rack and a test tube holder 15c can rotate with at least one rack or at least two holders mounted on the mechanism. The rotating mechanism for rotating a test tube rack and a test tube holder 15c can also change its rotational direction according to the kind and/or specifications of object mounted.

That is, the installation positions for the analyzers can be freely determined without being fixed with respect to the traveling directions of the carriers. See FIGS. 1 and 3.

However, the two different carriers, namely the test tube rack 22 and the test tube holder 21, cannot be mounted at one time on the rotating mechanism for rotating a test tube rack and a test tube holder 15c. This is because rotation in one direction uses one belt line mechanism.

Before either carrier is mounted on the rotating mechanism for rotating a test tube rack and a test tube holder 15c, therefore, whether the carrier is the test tube rack 22 or the test tube holder 21 needs to be discriminated each time.

Several methods are likely to be useable to conduct the discrimination. One of them is by using a device, such as a camera, that has a shape discrimination function, and it is common to use this method.

Since the test tube rack 22 and the test tube holder 21 significantly differ in shape, the discrimination between both is considered to be easy, but cost-related problems remain with the discrimination methods that use a device such as a camera. Considering costs, a far less expensive device can be constructed with the scheme that utilizes the carrier-stored RFIDs or equivalent in addition to sensors 25f to 25o.

A discrimination scheme by a functional unit for conveying-line carrier discrimination 201 which uses sensors and RFID information to discriminate the conveying line carriers is described below per FIGS. 5 to 8. Various patterns are considered to be useable. The following description relates only to four examples of applicable patterns. Additionally, the number and positions of sensors and the number of RFID information exchange antennas are not limited to the description.

Figure 5:
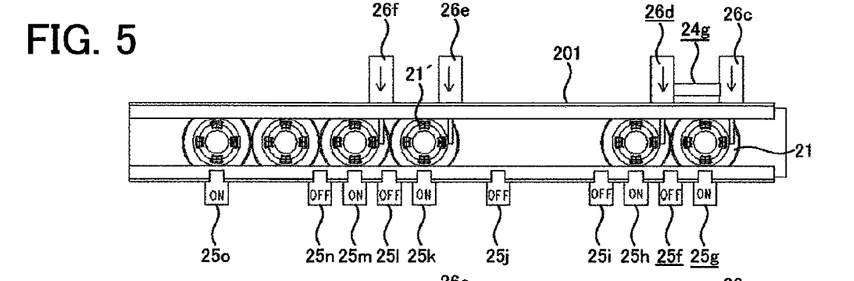
FIG. 5 is a top view showing a conveying line in a typical stopping pattern.

FIG. 5 shows an example in which an array of test tube holders 21 are in a stopped condition in front of the rotating mechanism for rotating a test tube rack and a test tube holder 15c. Usually, test tube holders 21 discriminate and operate at high speed, so the holders 21 become arrayed in this form, only in case of system abnormality. Buffers 15a, 15b can also be provided in front of the analyzers. In the event of abnormality, however, the line is controlled to stop after the sensor 25o has remained on for several tens of seconds in succession.

Since the belt line of the conveying line 15d usually operates without stopping, the belt line uses a stopper mechanism to control the operation of the racks and holders.

Referring to FIG. 5, a test tube holder 21 that has arrived at a stopper 26c on the conveying line 15d comes to a temporary stop there and exchanges information with the system via the antenna 24g.

At this time, the system can recognize that the carrier is a holder, since the information identifying the holder is stored within an ID chip mounted on the holder. In addition, since the sensor 25f is off and the sensor 25g is on, the system can determine that the carrier present in a stopped condition at the stopper 26c is reliably the test tube holder 21.

Upon the discrimination of the test tube holder 21, a stopper 26d operates to stop a following carrier (another test tube holder 21 or test tube rack 22), and stands by in this state.

By activating the above two stoppers alternately, the system can supply test tube holders 21 or test tube racks 22, one at a time, to the rotating mechanism for rotating a test tube rack and a test tube holder 15c.

If the following carrier is also a test tube holder 21, a stopper 26e operates and waits for an arrival of the carrier.

Figure 6:
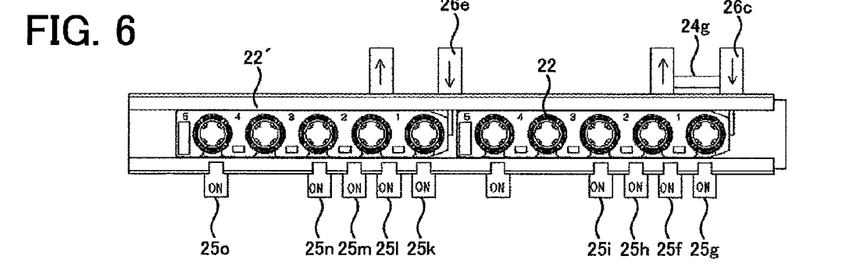
FIG. 6 is a top view showing a conveying line in another typical stopping pattern.

Referring to FIG. 6, a test tube rack 22 that has arrived at the stopper 26c on the conveying line 15d comes to a temporary stop there and exchanges information with the system via the antenna 24g. As in FIG. 5, this rack exchanges information with the system, and upon the system discriminating the test tube rack 22, the stopper 26e operates and waits for an arrival of a following carrier. In addition, the sensors 25f to 25i turn on. This enables the system to determine the test tube rack 22 to be in a stopped condition.

If the carrier that has next arrived is a test tube rack 22', the sensors 25k to 25o turn on, thus enabling the system to discriminate the test tube rack 22'. Upon two test tube racks 22 arriving in succession, the stoppers 26c and 26e operate alternately, enabling the test tube racks 22 to be supplied, one at a time.

Figure 7:
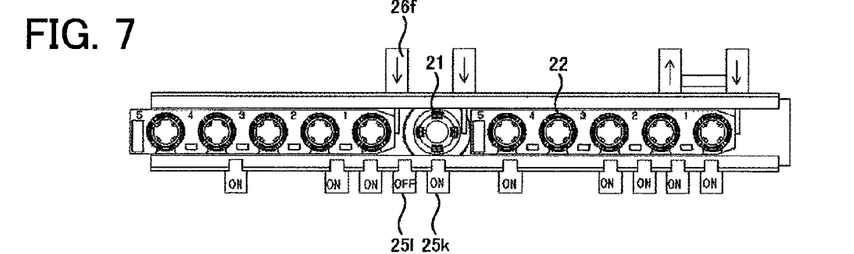
FIG. 7 is a top view showing a conveying line in yet another typical stopping pattern.

FIG. 7 shows an example in which, while a test tube rack 22 is the first carrier to arrive and is processed under the same conditions as in FIG. 6, the carrier that immediately follows is a test tube holder 21. The sensor 25k turns on and the sensor 25l turns off. Thus, the system can determine the standing-by carrier to be the test tube holder 21.

Upon the second standing-by carrier being determined to be the test tube holder 21, a stopper 26f operates and waits for an arrival of a following carrier.

Figure 8:
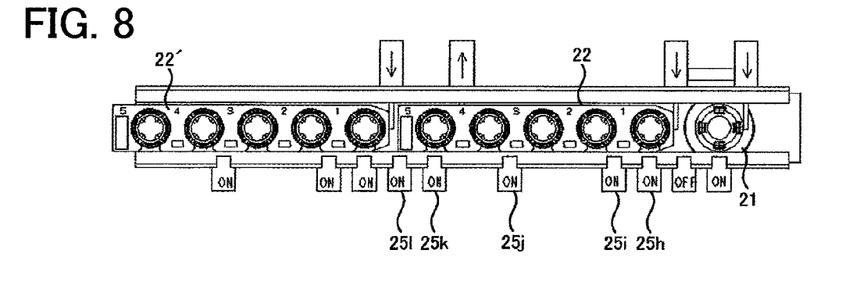
FIG. 8 is a top view showing a conveying line in a further typical stopping pattern.

FIG. 8 shows an example in which, while a test tube holder 21 is the first carrier to arrive and is processed under the same conditions as in FIG. 5, the carrier that immediately follows is a test tube rack 22. The sensors 25h to 25l turn on, enabling the system to determine the standing-by carrier to be the test tube rack 22.

Upon yet another standing-by carrier being determined to be a test tube rack 22', the stopper 26f operates and waits for an arrival of a following carrier.

Cases of the individual carrier discrimination to be executed before carriers move to the rotating mechanism for rotating a test tube rack and a test tube holder 15c have been described above. Various other patterns naturally exist. For example, referring to the number of sensors required for discrimination between test tube holders and test tube racks, if FIG. 5 is taken as an example, even in a case of two test tube holders arriving in concatenated form, arranging the sensors 25f and 25g so as to turn off the sensor 25f and turn on the sensor 25g enables the system to determine the two concatenated carriers to be test tube holders, since test tube holders and test tube racks significantly differ in shape. For test tube rack discrimination, the sensors 25f, 25g both turn on as shown in FIG. 6. That is, discrimination between test tube holders and test tube racks is possible by arranging at least two adjacent sensors. Adjacent sensors are desirably arranged at a spatial interval narrower than that of the test tubes on test tube holders in a case that two of the test tube holders are conveyed in succession with a test tube mounted on both of the two holders.

The sample conveying system is implemented that is also able to supply samples to each analyzer stably under a highly reliable state by executing carrier discrimination and information exchange in substantially the same way as the above, even on the rotating mechanism for rotating a test tube rack and a test tube holder 15c.

DESCRIPTION OF REFERENCE NUMBERS

11 Sample conveying system
12 Analyzer that receives test tube holders
13 Analyzer that receives test tube racks
14 Analyzer that receives test tube racks
15 Conveying line common to test tube racks and test tube holders
16 Dedicated rotating mechanism for test tube racks
11 Test tube holder
22 Test tube rack
23 Branching mechanism
24 Communications antenna
25 Carrier detection sensor
26 Stopper mechanism
27 Guide for preventing test tube holder overturn
28 Belt line
29 Test tube rack moving mechanism
201 Functional unit for conveying-line carrier discrimination

The invention claimed is:

1. A sample conveying system, comprising:
a line that conveys test tubes each containing a sample; and
a plurality of processing units each disposed along the conveying line, the units being inclusive of at least an analyzing unit, wherein
the conveying line includes:
a conveying belt line that conveys, in mixed form, a test tube rack holding the sample-containing test tubes together as one set, and a test tube holder holding one sample-containing test tube;
a mechanism that discriminates between the test tube racks and test tube holders conveyed to the conveying belt line;
a control unit that specifies analyzers to which the test tube racks and the test tube holders are to be supplied; and
at least two stoppers that each stop the test tube racks and the test tube holders, wherein
the test tube racks and test tube holders in a stopped condition in concatenated form on the conveying belt line are independently released from the stopped condition, one by one with the belt moving, by alternate or independent operation of the stoppers.

2. The sample conveying system according to claim 1, wherein
the test tube racks and the test tube holders each include a chip used to store information and data on the sample accommodated in each mounted test tube, on a conveyance destination of the sample, and on details of a process to be conducted upon the sample,
the conveying line includes a reader that reads the information stored on the chip, and
supply of the test tube racks and the test tube holders to the analyzers is based on the information read by the reader.

3. The sample conveying system according to claim 1, further comprising:
a first stopper, a second stopper, and a third stopper, for stopping the test tube rack and the test tube holder continuously conveyed on the conveying belt line, as the stopper, wherein
the first stopper and the second stopper are arranged at a spatial interval which is a same length of the test tube holder, and the first stopper and the third stopper arranged at a spatial interval which is a same length of the test tube rack, and
the control unit separates and conveys, individually, the test tube holder and the test tube rack conveyed continuously by controlling the operation of each stopper.

4. The sample conveying system according to claim 1, further comprising:
two or more sensors disposed adjacent the conveying belt line, wherein
the sensors include first sensors and second sensors for each of the stoppers,
the first sensor detects the existence of the test tube rack or the test tube holder stopped with the corresponding stopper, and
the second sensor detects which one of the test tube holder and the test tube rack is stopped by the corresponding stopper.

5. A sample conveying system, comprising:
a line that conveys test tubes each containing a sample; and
a plurality of processing units each disposed along the conveying line, the units being inclusive of at least an analyzing unit, wherein
the conveying line includes:
a conveying belt line that conveys, in mixed form, a test tube rack holding the sample-containing test tubes together as one set, and a test tube holder holding one sample-containing test tube;
a mechanism that discriminates between the test tube racks and test tube holders conveyed to the conveying belt line;
a control unit that specifies analyzers to which the test tube racks and the test tube holders are to be supplied; and
a discrimination device that discriminates a difference in external shape between the test tube racks and the test tube holders, wherein
the discrimination device is configured to:
function while the conveying belt line is in operation or in a stopped condition; and
convey the test tube racks and the test tube holders, one at a time, independently, even if the racks and the holders are in a stopped condition in concatenated form on the conveying belt line.

6. The sample conveying system according to claim 5, wherein
a first sensor and a second sensor are arranged at a spatial interval narrower than that of the test tubes on the test tube holders, and
the test tube holders, each with one of the test tubes mounted thereon, are continuously conveyed.

7. The sample conveying system according to claim 6, further comprising:
a determining means which, if the two sensors of the discrimination device differ in output value, determines that a sample holder is being conveyed.

8. A sample conveying system, comprising:
a line that conveys test tubes each containing a sample; and
a plurality of processing units each disposed along the conveying line, the units being inclusive of at least an analyzing unit, wherein the conveying line includes:
a conveying belt line that conveys, in mixed form, a test tube rack holding the sample-containing test tubes together as one set, and a test tube holder holding one sample-containing test tube;
a mechanism that discriminates between the test tube racks and test tube holders conveyed to the conveying belt line;
a control unit that specifies analyzers to which the test tube racks and the test tube holders are to be supplied; and
a mechanism that changes a traveling direction of the test tube racks and test tube holders on the conveying belt line by 90° in each of leftward and rightward directions, wherein
the mechanism includes a device that discriminates between the test tube racks and the test tube holders, and has a capacity to accept the test tube racks in units of at least one unit and the test tube holders in units of at least two units, one at a time, and
the mechanism is used to supply the test tube racks and the test tube holders, after each being 90° changed in the traveling direction, to the analyzers specified from the system or a host computer.

* * * * *